United States Patent [19]

McGowan et al.

[11] Patent Number: 5,053,623

[45] Date of Patent: Oct. 1, 1991

[54] PHOTOMETRIC ANALYZER FOR DIFFERENTIAL TOTAL REDUCED SULFUR MEASUREMENT BY COMPARISON WITH SAMPLE GAS

[75] Inventors: Gerald F. McGowan, Parker; Ronald L. Ketchum, Littleton; Allan L. Budd, Denver, all of Colo.

[73] Assignee: Lear Siegler Measurement Controls Corporation, Englewood, Colo.

[21] Appl. No.: 548,481

[22] Filed: Jul. 2, 1990

[51] Int. Cl.$^5$ ............................................. G01N 21/01
[52] U.S. Cl. ..................................... 250/373; 250/383; 250/565
[58] Field of Search ............... 250/372, 373, 383, 565, 250/461.1, 458.1; 422/91; 356/439

[56] References Cited

U.S. PATENT DOCUMENTS

| | | | |
|---|---|---|---|
| 3,796,887 | 3/1974 | Vincent et al. | 250/565 |
| 3,845,309 | 10/1974 | Helm et al. | 250/365 |
| 3,969,626 | 7/1976 | Saltzman | 250/344 |

FOREIGN PATENT DOCUMENTS 61-243343  10/1986  Japan ................................. 250/373

OTHER PUBLICATIONS

Lear Siegler Measurement Controls Corporation Brochure, "The Extractive System"; 2/89.

Primary Examiner—Constantine Hannaher
Assistant Examiner—Jacob M. Eisenberg
Attorney, Agent, or Firm—Fields, Lewis, Pittenger & Rost

[57] ABSTRACT

A photometric analyzer for measuring differential total reduced sulfur in a sample gas stream is provided. It includes a supply for a sulfur bearing gas sample, an oven having an inlet connected to the supply for converting TRS to $SO_2$ and an outlet through which the gas sample is discharged. A valve is connected to the outlet of the oven. An $SO_2$ bypass line is connected between the supply and the valve. A sample cell with transparent ends has an inlet adjacent one end connected to the valve for alternately receiving sample gas from either the oven or the bypass line and has an outlet adjacent the other end. A pump connected to the sample cell outlet draws the gas sample through the sample cell. A light source at the one end of the sample cell directs light of a predetermined wave length through the sample cell. A light sensing device at the other end detects the amount of light passing through the sample cell at any given time and provides an output signal to an analyzer. The analyzer determines the TRS in the gas sample. Zero air is supplied to the valve so that the zero air can be cycled into the sample cell for measurement by the analyzer to determine $SO_2$ levels in the sample gas. A heat exchanger assures that each of the gases and air are at a constant temperature. The pressure of the gases and air is held at a constant pressure as they pass through the sample cell by a pressure regulator.

21 Claims, 1 Drawing Sheet

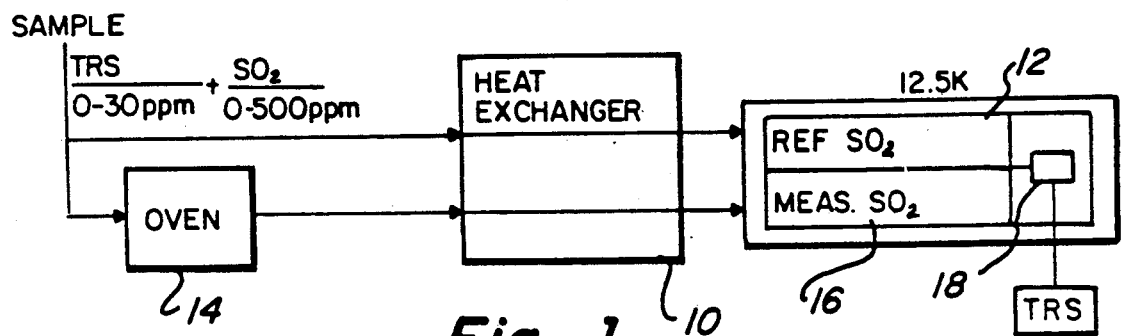
Fig_1
PRIOR ART
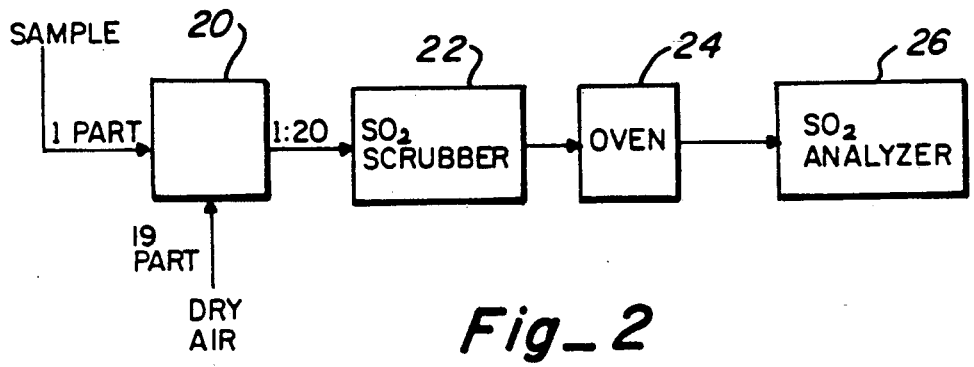
Fig_2
PRIOR ART
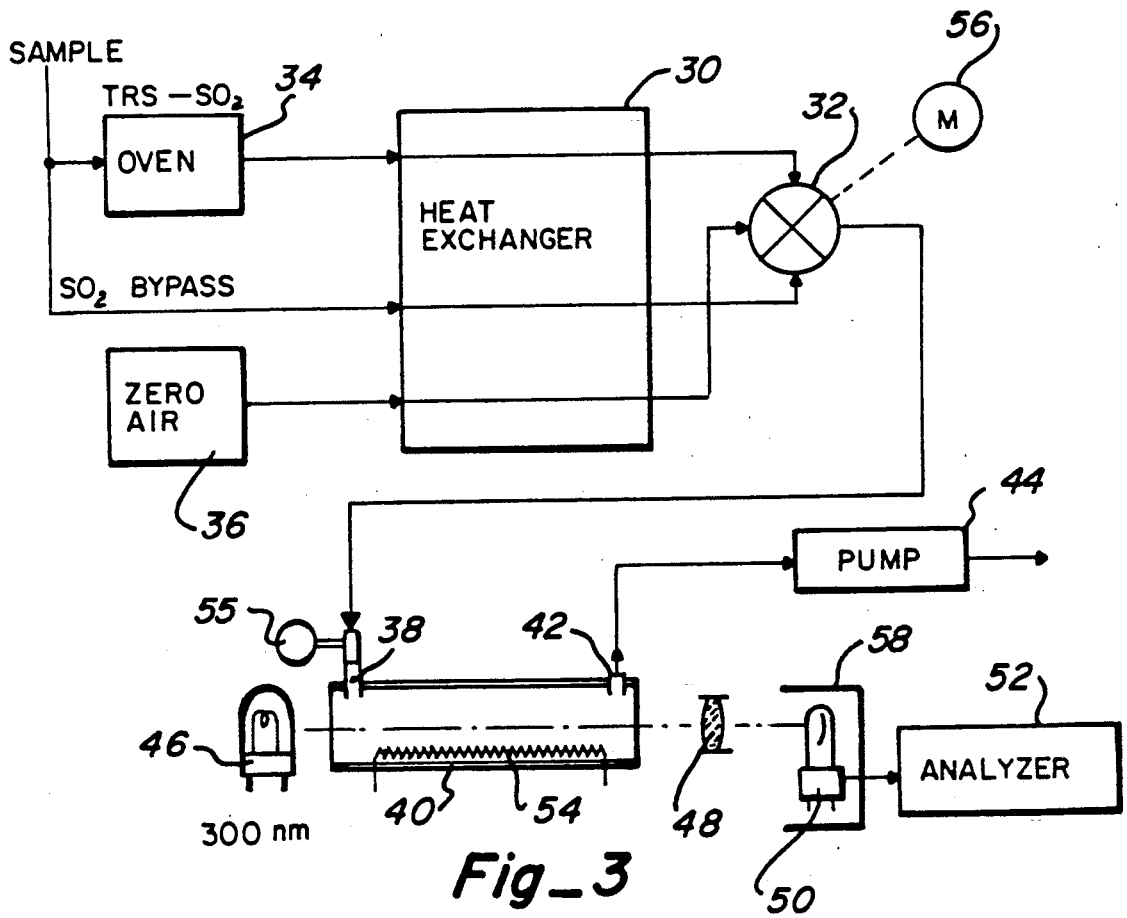
Fig_3

PHOTOMETRIC ANALYZER FOR DIFFERENTIAL TOTAL REDUCED SULFUR MEASUREMENT BY COMPARISON WITH SAMPLE GAS

TECHNICAL FIELD

This invention relates to an apparatus and method for measuring low levels of total reduced sulfur (TRS) in a gas mixture containing high levels of sulfur dioxide. The apparatus and method also contemplates measuring the background levels of sulfur dioxide ($SO_2$) in the gas mixture.

BACKGROUND ART

It is necessary to monitor gases from smoke stacks in industrial plants to be sure that the levels of TRS and $SO_2$ are within governmental performance specifications. One device which has been used for this purpose is the "TRS Extractive System" manufactured by Lear Siegler Management Controls Corporation of Englewood, Colorado. In this device, the gas sample extracted from the stack is split into two streams. One stream flows continuously through a reference section of a sample cell, providing a reference, or common mode $SO_2$ level equal to the process $SO_2$ concentration. The other portion of the extracted gas stream passes through a thermal oxidizing furnace where TRS compounds are oxidized to $SO_2$. The gas stream exiting the furnace contains the process $SO_2$ concentration plus the $SO_2$ resulting from the oxidized TRS. This stream flows continuously through the measurement section of the cell. The detector then senses the difference in attenuated light intensity as the light beam is alternated between the measurement and reference portions of the sample cell. The difference signal is proportional to the $SO_2$ produced by oxidizing the TRS compound. Thus, the analyzer measures the TRS concentration directly in the presence of a high common mode level of $SO_2$ without measuring the individual $SO_2$ levels. The instrument can be automatically adjusted to compensate for the effects of line voltage variation, lamp and detector aging, and varying concentrations of background $SO_2$. However, changes cannot be measured in the precipitate that collects in the cells. Since each cell will have contaminate build-up at different rates, over a period of time the accuracy of the device will decrease.

Another type of analyzer is one in which the sample gas is diluted and then passed through an $SO_2$ scrubber and oven before being introduced into a single $SO_2$ analyzer. While this apparatus overcomes the disadvantage of using two cells, the $SO_2$ scrubber is quite expensive and must be replaced frequently because of the levels of $SO_2$ found in TRS monitoring applications.

DISCLOSURE OF THE INVENTION

In accordance with this invention, a photometric analyzer for measuring differential total reduced sulfur in a sample gas stream is provided. It includes means for supplying a sulfur bearing gas sample, an oven having an inlet connected to the supplying means for converting TRS to $SO_2$ and having an outlet through which the gas sample is discharged. Valve means are connected to the outlet of the oven. An $SO_2$ bypass line is connected between the supplying means and the valve means. A generally cylindrical sample cell having an inlet adjacent one end is connected to the valve means for alternately receiving sample gas from either the oven or the bypass line and having an outlet spaced from the inlet and adjacent the other end thereof, the first and second ends being transparent. A pump is connected to the sample cell outlet to draw the gas sample through the sample cell. A light source is mounted at the one end of the sample cell for directing light of a predetermined wave length through the sample cell. A light sensing device is mounted at the other end of the sample cell for detecting the amount of light passing through the sample cell at any given time. An analyzer is connected to the light sensing device to provide differential light measurements of samples from the oven and from the bypass line to determine the total reduced sulfur in the gas sample. Means can be provided for supplying zero air to the valve means so that the zero air can be cycled into the sample cell for measurement by the analyzer to determine $SO_2$ levels in the sample gas. The heat exchanger can be mounted between the valve means and each of the oven, the $SO_2$ bypass line and the zero air supplying means so that each of the gases and air passes therethrough to minimize condensation. Also, a pressure regulator at the inlet of the sample cell assures that each sample passing through the cell is at the same pressure.

Additionally, the light source can transmit light at a wavelength of approximately 300 nm. A filter can be provided between the other end of the sample cell and the light sensing device to transmit only light having a wavelength of 300 nm. A heater may be provided in the sample cell to minimize condensation therein. Furthermore, a solar blind can be positioned around the light sensing device to block all light from the light sensing device except light from the light source.

The invention contemplates a method of determining the amount of total reduced sulfur in the gas sample. This method includes the steps of providing a first sample gas to be analyzed, passing some of the first sample gas through an oven to oxidize the TRS in the first sample gas to $SO_2$ to form a second sample gas, providing a generally cylindrical sample cell having first and second transparent ends, drawing the first and second samples through the sample cell from the first end to the second end in alternating cycles, directing a light beam through the sample cell from the first end and through the second end of desired wavelength. The method may further include the steps of detecting at the second end the amount of light transmitted through the sample cell during each cycle of the first and second samples as they are alternately drawn to the sample cell, comparing the difference in the light detected during each cycle and determining the amount of TRS in the first sample from the differences in detected light associated with each cycle.

The method can include the further steps of passing the first and second samples through a heat exchanger before drawing them through the sample cell to minimize condensation within the samples and to maintain all sample streams at the same temperature. Additionally, each sample is maintained at the same pressure as every other sample.

The method contemplates the further step of drawing zero air through the sample cell after a predetermined number of cycles, comparing the difference in light detected from the first sample and the zero air and determining the amount of $SO_2$ in the first sample from the difference in detected light associated with the first sample and the zero air. A light beam may be used having a wavelength of 300 nm and each cycle may have a duration from five seconds to five minutes, five seconds being preferred. The zero air may be drawn through the sample cell after every third or fourth cycle. The sample cell may be heated to minimize condensation of gases passing therethrough.

Additional advantages of this invention will become apparent from the description which follows, taken in conjunction with the accompanying drawings.

BRIEF DESCRIPTION OF THE DRAWINGS

FIG. 1 is a diagrammatical view of one prior art device for measuring TRS;

FIG. 2 is a diagrammatical view of another device for measuring TRS; and

FIG. 3 is diagrammatical view of the present invention.

BEST MODE FOR CARRYING OUT THE INVENTION

In order to best understand the advantages of the present invention, a brief look at two prior art devices will be helpful. The first is shown in FIG. 1 wherein a sample is split into two streams, one stream passing directly to a heat exchanger 10 and into a sample cell 12 which provides a reference rating indicative of the amount of $SO_2$ in the sample stream. The other half of the stream passes through an oven which converts the total reduced sulfur in the sample to $SO_2$. This sample stream then passes through heat exchanger 10 to sample cell 16 which measures the $SO_2$ in that stream. By comparing these streams with an analyzer 18, a reading will be given which shows the amount of total reduced sulfur in the sample. This method is very expensive and has a long term drop in accuracy due to the dual sample cells becoming contaminated at different rates.

In another prior art device shown in FIG. 2, a sample is supplied to a mixing chamber wherein one part of the sample is mixed with nineteen parts of dry air to give a 1:20 ratio. This stream is then fed to an $SO_2$ scrubber 22 which removes the $SO_2$ in the sample. Next the sample is passed through an oven 24 which combusts the TRS to $SO_2$ which is then measured in an $SO_2$ analyzer 26. The requirements to scrub the $SO_2$ and dilute the sample adds cost and complexity to the analyzer and has the potential of altering the TRS content of the gas sample. Furthermore, the scrubber requires frequent replacement at levels of $SO_2$ found in TRS monitoring applications.

Turning now to the present invention, which is illustrated in FIG. 3, it will be seen that a sample is divided so that one half of the sample passes directly through a heat exchanger 30 to a valve means 32 in the form of a three-way valve. Another portion of the sample passes through oven 34 wherein the TRS is converted to $SO_2$. This sample then passes through the heat exchanger 30 to valve 32. Also, a source of zero air 36 may be provided which also is supplied to valve 32. By passing each gas sample through heat exchanger 30, the temperature of each gas sample can be maintained at the same uniform temperature. The term "zero air" as used herein means a supply of gas which has no $SO_2$ in it. By selective positioning of valve 32, gases from any one of these three sources can be provided to the inlet 38 of sample cell 40 where it is pulled through the sample cell and outlet 42 by means of a vacuum pump 44. Sample cell 40 is typically about four inches long and has transparent ends. At a first end, a light source 46 is provided and transmits light through the sample cell past a filter 48 to a light sensing device 50 which provides an output signal to an analyzer 52. Conveniently, a heater 54 is provided within sample cell 40 to minimize the possibility of condensation within the cell. Conveniently, a pressure regulator 55 is provided adjacent inlet 38 so that each gas sample passing through cell 40 will be at the same pressure. Thus, by means of heat exchanger 30 and pressure regulator 55, each gas sample will be at the same uniform temperature and pressure to assure readings by analyzer 52 which are not adversely affected by temperature and pressure changes.

Suitable motor or solenoid 56 is provided for cycling valve 32 so as to alternately provide samples which have passed through the oven and samples which have not passed therethrough to the sample cell. The solenoid can be set to cycle over time periods ranging from five seconds to five minutes, five seconds having been found to be quite suitable. The attenuation of the light beam from light source 46 will be detected by light sensor 50 causing a difference in the signal provided to analyzer 52 during the cycle in which the sample which is passed through the oven is passing through the sample cell and the cycle in which the sample which is not passed through the oven passes through the sample cell. This provides a measurement of the TRS in the sample. Periodically, such as every three or four cycles, solenoid 56 will move valve 32 to a position providing a sample of zero air to the sample cell 40 which is compared with the bypass sample gas by the analyzer 52 providing a reading of the amount of $SO_2$ in the sample.

Typically, the light source has a wavelength of 300 nm. Similarly, filter 48 is provided which filters out any light not at this desired frequency. Also, a solar blind 58 can be provided around light detector 50 so that it receives no light other than that received from light source 46.

With this arrangement, it can be seen that the present invention has the advantages of both of the prior art devices without any of the disadvantages. The samples all pass through a common heat exchanger 30 to minimize condensation and to cause each gas sample to be at the same uniform temperature. A pressure regulator also assures that each gas sample is at the same pressure. The samples pass through a single sample cell which compares each sample so that any soiling of the sample cell will be equal for all readings. Furthermore, it is not necessary to dilute the sample gas nor utilize an expensive $SO_2$ scrubber.

This invention has been described in detail with reference to a particular embodiment thereof, but it will be understood that various other modifications can be effected within the spirit and scope of this invention.

What is claimed is:

1. A photometric analyzer for measuring differential total reduced sulfur in a sample gas stream, said analyzer comprising:
   means supplying a sulfur bearing gas sample;
   an oven, having an inlet connected to said supplying means, for converting total reduced sulfur to $SO_2$ and having an outlet through which the oven gas sample is discharged;
   valve means connected to said outlet of said oven;
   an $SO_2$ bypass line connected between said supplying means and said valve means;
   means for alternatingly discharging said oven gas sample and $SO_2$ bypass gas from said valve means;

a generally cylindrical sample cell having an inlet adjacent one end connected to said valve means for alternately receiving sample gas from either said oven or said bypass line and having an outlet spaced from said inlet and adjacent the other end thereof, said first and second ends each being transparent;

a pump connected to said sample cell outlet to draw the gas sample through said sample cell;

a light source mounted at said one end of said sample cell for directing light of a predetermined wavelength along said sample cell;

a light sensing device mounted at said other end of said sample cell for detecting the amount of light passing through said sample cell at any given time; and an analyzer connected to said light sensing device to provide differential light measurements of samples from said oven and from said bypass line to determine the total reduced sulfur in the gas sample.

2. Apparatus, as claimed in claim 1, wherein: said valve means is a three-way valve.

3. Apparatus, as claimed in claim 1, further including: means supplying zero air to said valve means so that zero air can be cycled into said sample cell for measurement by said analyzer to determine $SO_2$ levels in the sample gas.

4. Apparatus, as claimed in claim 3, further including: a heat exchanger mounted between said valve means and each of said oven, said $SO_2$ bypass line and said zero air supplying means so that each of said gases and air pass therethrough to minimize condensation therein and to maintain the same uniform temperature in the gases and air.

5. Apparatus, as claimed in claim 3, wherein: said light source transmits light having a wavelength of approximately 300 nm.

6. Apparatus, as claimed in claim 5, further including: a filter between said other end of said sample cell and said light sensing device to transmit only light having a wavelength of 300 nm.

7. Apparatus, as claimed in claim 3, further including: a heater in said sample cell to minimize condensation therein.

8. Apparatus, as claimed in claim 3, further including: a pressure regulator adjacent said cell inlet to maintain the same pressure in the gases and air passing through said cell.

9. Apparatus, as claimed in claim 3, further including: a solar blind positioned around said light sensing device to block all light from said light sensing device except light from said light source.

10. A photometric analyzer for measuring differential total reduced sulfur in a sample gas stream, said analyzer comprising:

means supplying a sulfur bearing gas sample;

an oven, having an inlet connected to said supplying means, for converting total reduced sulfur to $SO_2$ and having an outlet through which the oven gas sample is discharged;

a three-way valve connected to said outlet of said oven;

an $SO_2$ bypass line connected between said supplying means and said valve means;

means supplying zero air to said valve means so that zero air can be cycled into said sample cell for measurement by said analyzer to determine $SO_2$ levels in the sample gas;

a heat exchanger mounted between said valve means and each of said oven, said $SO_2$ bypass line and said zero air supplying means so that each of said ; gases and air pass therethrough to minimize condensation;

means for alternately discharging said oven gas sample and said $SO_2$ bypass gas from said valve means and selectively discharging said zero air from said valve means;

a generally cylindrical sample cell having an inlet adjacent one end connected to said valve means for alternately receiving sample gas from either said oven or said bypass line and having an outlet spaced from said inlet and adjacent the other end thereof, said first and second ends each being transparent;

a heater in said sample cell to minimize condensation therein;

a light sensing device mounted at said other end of said sample cell for detecting the amount of light passing through said sample cell at any given time;

a solar blind positioned around said light sensing device to block all light from said light sensing device except light from said light source; and an analyzer connected to said light sensing device to provide differential light measurements of samples from said oven and from said bypass line to determine the total reduced sulfur in the gas sample.

11. Apparatus, as claimed in claim 10, further including:
a pressure regulator adjacent said cell inlet to maintain the same pressure in the gases and air passing through said cell.

12. Apparatus, as claimed in claim 10, further including:
a filter between said other end of said sample cell and said light sensing device to transmit only light having a wavelength of 300 nm.

13. A method of determining the amount of total reduced sulfur in a gas sample, said method comprising the steps of:

providing a first sample gas to be analyzed;

passing some of the first sample gas through an oven to reduce the total reduced sulfur in the first sample gas to $SO_2$ to form a second sample gas;

providing a generally cylindrical sample cell having first and second transparent ends;

drawing the first and second samples through the sample cell from said first end to said second end in alternating cycles;

directing a light beam through the sample cell from the first end and through the second end of a desired wavelength;

detecting at the second end the amount of light transmitted through the sample cell during each cycle of the first and second samples as they are alternately drawn through the sample cell;

comparing the difference in the light detected during each cycle; and determining the amount of total reduced sulfur in the first sample from the differences in detected light associated with each cycle.

14. A method, as claimed in claim 13, including the further step of:
maintaining the first and second samples at the same temperature and pressure when drawing them through the sample cell.

15. A method, as claimed in claim 13, including the further steps of:

drawing zero air through the sample cell after a predetermined number of cycles;

comparing the difference in light detected from the first sample and the zero air; and determining the amount of $SO_2$ in the first sample from the difference in detected light associated with the first sample and the zero air.

16. A method, as claimed in claim 15, including the further step of:

maintaining the first and second samples and the zero air at the same temperature and pressure when drawing them through the sample cell.

17. A method, as claimed in claim 13, wherein:

the light beam has a wavelength of 300 nm.

18. A method, as claimed in claim 13, wherein:

each cycle has a duration from five seconds to five minutes.

19. A method, as claimed in claim 18, wherein:

each cycle has a duration of five seconds.

20. A method, as claimed in claim 15, wherein:

the zero air is drawn through the sample cell after every three or four cycles.

21. A method, as claimed in claim 13, including the further step of:

heating the sample cell to minimize the condensation of gases passing therethrough.

* * * * *